(12) United States Patent
Barr

(10) Patent No.: US 8,517,974 B2
(45) Date of Patent: Aug. 27, 2013

(54) PROGRAMMABLE DEVICE FOR TREATING OVER DRAINAGE DUE TO SIPHONIC EFFECTS IN HYDROCEPHALUS SHUNT SYSTEMS

(75) Inventor: Richard Henry Howard Barr, Torquay (GB)

(73) Assignee: Centrax Limited, Devon (GB)

( * ) Notice: Subject to any disclaimer, the term of this patent is extended or adjusted under 35 U.S.C. 154(b) by 0 days.

(21) Appl. No.: 13/462,890

(22) Filed: May 3, 2012

(65) Prior Publication Data
US 2012/0302937 A1 Nov. 29, 2012

(30) Foreign Application Priority Data

May 24, 2011 (GB) .................................. 1108720.2

(51) Int. Cl.
*A61B 19/00* (2006.01)
(52) U.S. Cl.
USPC .................................................. 604/9; 604/8
(58) Field of Classification Search
None
See application file for complete search history.

(56) References Cited

U.S. PATENT DOCUMENTS

| | | | |
|---|---|---|---|
| 2,570,228 A | 10/1951 | Grundstrom | |
| 3,889,687 A | 6/1975 | Harris et al. | |
| 4,772,257 A | 9/1988 | Hakim et al. | |
| 5,643,194 A | 7/1997 | Negre | |
| 2002/0066486 A1 | 6/2002 | Sett | |
| 2004/0122348 A1 | 6/2004 | Hokanson et al. | |
| 2007/0093741 A1* | 4/2007 | Miethke | 604/9 |
| 2009/0093741 A1 | 4/2009 | Lach | |

FOREIGN PATENT DOCUMENTS

| | | |
|---|---|---|
| DE | 810909 C | 8/1951 |
| DE | 19535637 A1 | 3/1997 |
| EP | 1677321 A1 | 7/2006 |

OTHER PUBLICATIONS

European Search Report, Application No. EP12164630.1, Dated Jul. 30, 2012.
Intellectual Property Office Search report under Section 17(5), Application No. GB1108720.2, Dated Sep. 19, 2011.

* cited by examiner

*Primary Examiner* — Leslie Deak
*Assistant Examiner* — Sara Sass
(74) *Attorney, Agent, or Firm* — MacMillian, Sobanski & Todd, LLC

(57) ABSTRACT

A valve assembly for adjusting the flow of bodily fluid from one part of a human body to another includes a body portion having a flow inlet and a flow outlet. A valve located in a flow path from the inlet to the outlet includes a valve seat and a closing element that is adapted to seal against the valve seat. A carrier element is mounted within the body portion and has a plurality of pockets. Each pocket houses a respective preload element, wherein each preload element is of a different weight from that of the other preload elements. The carrier element is moveable relative to the body portion so as to align a preload element of a desired weight with the closing element. The self weight of the chosen preload element applies a preload to the closing element dependent on the orientation of the valve assembly.

20 Claims, 1 Drawing Sheet

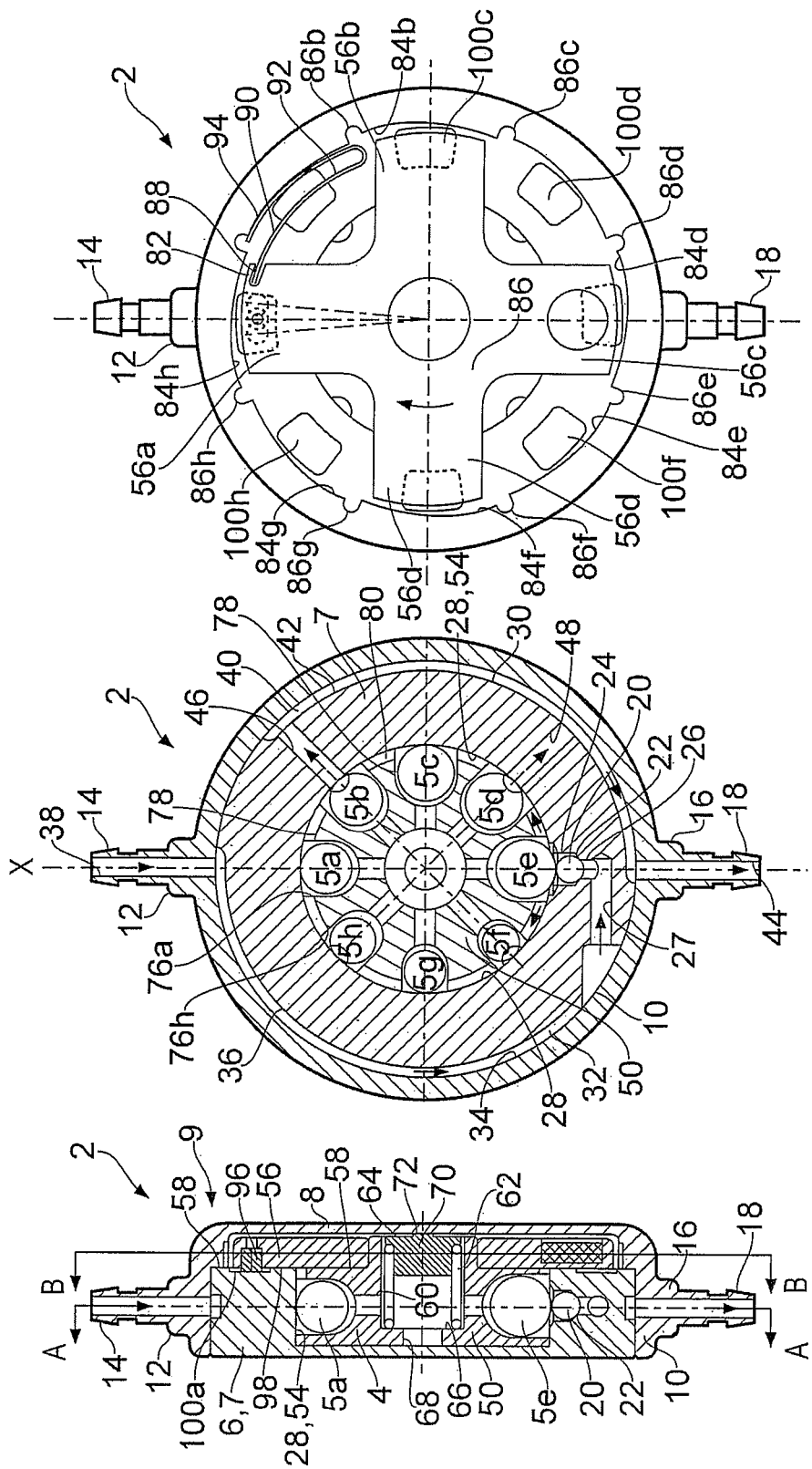

PROGRAMMABLE DEVICE FOR TREATING OVER DRAINAGE DUE TO SIPHONIC EFFECTS IN HYDROCEPHALUS SHUNT SYSTEMS

BACKGROUND OF THE INVENTION

This invention relates to a valve for adjusting the flow rate of cerebral spinal fluid. Particularly, although not exclusively, it relates to an adjustable anti-siphon device for preventing over drainage in shunted hydrocephalic patients.

Hydrocephalus is a defective condition of the brain caused by an imbalance between production of cerebral spinal fluid (CSF) within the brain and the capacity of the brain to re-absorb such fluid at normal pressure. Hydrocephalus may be congenital, accidental or age related and can result in loss of a wide range of physical and mental faculties. The accepted method of treatment of the condition is to divert excess fluid which the brain, through its impairment, is unable to absorb, to some other part of the body such as the right atrium of the heart or the peritoneal cavity, where the fluid can re-enter the blood stream. The primary technical challenge associated with this method of treatment is developing the capacity to control the conditions of pressure and flow within the brain in such a manner as to enable lost faculties to be restored, depending on the severity of the condition. This challenge is exacerbated by the greatly differing range of impairment between different patients in different body positions.

Various valve assemblies have been developed to control the pressure and flow conditions within the brain to desired levels. Such devices are commonly known as valves. If the flow imbalance referred to above is not addressed, pressure within the brain rises to an abnormal level. Such increased pressure causes the ventricles of the brain to expand and causes abnormal stress and damage within the brain tissue. Consequently, many valves focus on a technology that controls the pressure within the ventricles of the brain directly, restricting that pressure to a desired level and allowing flow rates to vary to accommodate the target pressure. Such devices are referred to as pressure control valves and commonly comprise an orifice that may be forced open by fluid pressure within the brain against some form of resistant mechanism such as a ball and spring or a slit in a tubular member. The majority of valves in use at the present time are pressure control valves. However other types of valve based on flow control rather than pressure control have been and are being developed and may offer certain advantages over the pressure control type in due course.

Due to changes in body posture from horizontal to vertical the application of any of the above types of valve becomes much more difficult to control when the shunt system drains into the abdominal cavity, rather than into the heart, which former option is the preferred choice for most clinicians on the grounds of simplification of surgery and consequences of possible infection. This has led to the development of a range of devices generally referred to as anti-siphon devices being developed to eliminate or mitigate the over drainage effect where drainage takes place into the abdominal cavity. These devices are included in the shunt system in addition to the above mentioned valves which are basically designed to control pressure or flow when the body position is horizontal.

One such type of anti-siphon device based on the principle of ball and orifice for controlling pressure, relies on the force of the ball on its seating being accomplished not by a spring but by the gravitational effect of the ball itself, or with the additional effect of further balls, when the device is disposed in the vertical, or part vertical, position as defined by inlet and outlet. Depending on the total gravitational weights of these balls so the force of the ball on the orifice is increased as the patient moves vertically and the overall pressure drop of the system is thereby increased.

An example of such a device is described in U.S. Pat. No. 3,889,687 filed Jan. 31, 1974. In this device the main pressure control valve and the anti-siphon element are contained in a single casing.

Whilst this idea represents a very great improvement in control it is a fixed system and still does not allow for the large differences which occur between individuals of different statures and abdominal sizes. For example, when vertical, the height distance between the zero pressure point in the abdominal cavity and the right atrium which is generally regarded as zero pressure datum for all body positions, can vary from less than 10 cm water head in a small child to more than 30 cm in a tall adult. The difference of 20 cm or more far exceeds the normal intra-cranial pressure values.

Some additional variability of control, therefore, is appropriate, in order to optimize the anti-siphon treatment in different individuals. One such way of doing this is exemplified in U.S. Pat. App. No. 2007/0093741/A which uses the gravitational ball principles of U.S. Pat. No. 3,889,687 in conjunction with a controllable spring to modify the gravitational effect of the ball and thereby achieve variability in the pressure setting of the valve so that the setting can be optimized for different individuals.

The invention submitted in this document provides by means of the programmed application of different gravitational components a method of controlling over drainage in a shunt system due to siphonic effects when the human body position is other than horizontal.

According to a first aspect of the present invention, there is provided:
  a valve assembly for adjusting the flow of bodily fluid from one part of a human or animal body to another, the valve assembly comprising:
  a body portion having a flow inlet and a flow outlet;
  a valve located in a flow path from the inlet to the outlet, the valve comprising a valve seat and a closing element, the closing element being adapted to seal against the valve seat;
  a carrier element mounted within the body portion, having a plurality of pockets, each pocket housing a respective preload element, each preload element being of a different weight from that of the other preload elements; and
  the carrier element being moveable relative to the body portion, so as to align a preload element of a desired weight with the closing element, the self weight of the chosen preload element applying preload to the closing element dependent on the orientation of the valve assembly.

The valve assembly may be made from bio-compatible material, may be suitable for implantation within the human body and may be adjustable from outside the human body.

The closing element may have any suitable shape to assist in sealing and allow the closing element to move easily from a position in which it engages and seals with the valve seat to a position in which it is disengaged. For example, that part of the surface of the closing element which engages with a circular valve seat may be spherical, planar or conical.

Each preload element may have any suitable shape to allow it to move easily from a position in which it engages the closing element to a position in which it is disengaged. For example, each preload element may be substantially spherical, substantially cylindrical or substantially rectilinear.

The closing element and/or the preload elements may be formed from high density material such as tungsten carbide or tantalum.

The carrier element may be in the form of a rotary element or rotor having a plurality of pockets radially disposed around its rotational axis, each pocket housing a respective radially moveable preload element, each preload element being of a different weight from that of the other preload elements; and the rotary element being rotatable relative to the body portion, so as to align a preload element of a desired weight with the closing element, the self weight of the chosen preload element when its centre of mass is above the valve seat applying preload to the closing element dependent on the orientation of the valve assembly, the range of weights provided by the plurality of preload elements providing a range of preloads on the closing element such that any particular preload within the range may be chosen by appropriate rotation of the rotary element relative to the body portion.

In one embodiment, the valve assembly is used for controlling over drainage in a shunt system due to siphonic effects when the human body position/posture is other than lying horizontal. The assembly may be implanted under the skin of the human body and may be attached at its inlet and/or outlet to other parts of the shunt system. According to another aspect of the present invention, the valve assembly may comprise, as described previously, a body portion, a gravity operated differential pressure valve and a carrier element in the form of a rotary element or rotor.

The valve assembly may have a differential pressure valve with a circular seating located within a substantially circular body portion. The closing member for sealing the orifice of the valve may be a closing ball fitting to the seating and manufactured from high density material such as tungsten carbide or tantalum. The body portion may be oriented by implantation in such a manner that the first ball is situated vertically above the orifice when the human body posture is erect, producing a sealing force in a downward direction on the orifice due to the gravitational weight of the closing ball. Additional preload balls of different size and hence weight may be provided within the rotary element or rotor located concentrically within the circular body portion such that when the rotor is rotated to a selected position within the body portion a selected preload ball can be positioned accurately relative to the closing ball to produce a selected weight on the orifice which in turn produces a selected pressure characteristic from the orifice. The number of preload balls situated radially within the rotor define the number of pressure settings of the device. It should be understood that the reason the closing ball is smaller than the preload ball is to minimize the size of the device. Size predicates that the control orifice should be as small as practicable to deal with the amount of cerebral spinal fluid involved. Maintaining an optimum seal geometry dictates that the closing ball should also be small sized to suit the orifice. The weight of this closing ball alone under these criteria is insufficient to produce the required pressure characteristic from the orifice requiring an additional second substantially larger preload ball to provide the necessary gravitational force when added to the weight of the closing ball.

Part of the preload on the closing ball may be provided in a manner other than from preload balls within the rotor. For example one or more balls may be located co-axially with the sealing ball in a permanent manner so that a permanent portion of preload is applied to the closing ball, other than the variable portion provided from the selected preload ball within the rotor.

The rotor may be positionally controlled from outside the human body by applying a torque force to the rotor. This can be accomplished in a number of different ways including physically operating an indexing mechanism by finger pressure transcutaneously through a diaphragm which forms part of the outside wall of the body portion. However, a preferred way of positional control which reduces the possibility of an accidental change of setting is to apply the appropriate torque to the rotor by magnetic means externally applied from outside the human body.

A first way of achieving this would be to make the rotor of magnetic responsive material arranged in such a way as to allow the magnetic torque to be applied directly to the rotor via a magnetic controller externally operated in rotating manner. A second way of achieving magnetic control from outside the human body would be to apply a torque to the rotor via a ratchet mechanism whereby an axial movement of an external magnetic controller produces an axial force on a moveable magnetically responsive element within the rotor which is converted into a torque on the rotor by means of the ratchet mechanism.

Dealing with the first way of magnetic control, the rotary element would at least partially be made from or include magnetically responsive material and would comprise a plurality of defined pole pieces which extend parallel to the axis of the rotary element. The rotary element may be biased towards the body portion with a compression spring, for example, and may have a magnetic marker, the position of which would help to identify the position of the rotor relative to the body portion by means of a compass type device.

A compass positional setting device may be used to set the position of the carrier element or rotor relative to the body portion. An important requirement in the correct functioning of the device is that when the rotor is rotated to a particular point within the body portion the alignment of the preload ball with respect to the axis of the orifice valve must be fairly precise to enable correct contact between the preload and closing balls to take place. Otherwise, the gravitational effect could be compromised. A compass positional setting alone might not be sufficient to guarantee this requirement. Accordingly in addition to the compass setting it is proposed to identify the position of the rotor by means of a ratchet mechanism. A leaf spring attached to the rotor contacts a circular inner surface of the body portion which contains a number of detents or depressions which engage with the end of the leaf spring to limit rotation of the rotor in one direction so that if the number of notches corresponds to the number of balls and are spaced accordingly the position of the rotor can be determined by rotating the housing until the spring engages a notch which may be verified by hearing a click. The final location of the rotor relative to the body portion is determined by allowing it to have a small amount of axial movement relative to the body portion and is spring loaded axially on to its seating within the body portion by means of a central helical spring. A small pin protrusion attached to the rotor engages one of a number of depressions in the seating corresponding to the number of ball positions, thereby limiting the movement of the rotor in both directions when the rotor is on its seating. When the external magnetic force is applied the rotor is moved axially from its seating by magnetic attraction, thereby disengaging the pin from the depression and allowing the rotor to be moved rotationally to the appropriate circumferential position verified by the unidirectional action of the leaf spring as well as by spring engagement noise and compass reading. It should be understood that the pin protrusion from the rotor alone completely identifies the position of the rotor within the limits of the depression but that the leaf spring assists in achieving and identifying that position.

The previously described embodiment, may be combined, if appropriate, within a single body portion with other parts of the shunt system including, for example, a resistance valve or a differential pressure valve.

Various aspects of this invention will become apparent to those skilled in the art from the following detailed description of the preferred embodiment, when read in light of the accompanying drawings.

BRIEF DESCRIPTION OF THE DRAWINGS

FIG. 1 is a cross section through a valve assembly in accordance with the present invention;

FIG. 2 is a section on the line A-A of FIG. 1; and

FIG. 3 is a section on the line B-B of FIG. 1.

DETAILED DESCRIPTION OF THE PREFERRED EMBODIMENT

Referring to the drawings, a valve assembly 2 comprises a rotary element 4 housing a plurality of preload elements in the form of balls 5a to 5h. The rotary element 4 is mounted for rotation within a body portion comprising a substantially solid annular element 7 and a casing 9 which is integral with or attached to the annular element 7. The casing 9 is cup shaped and consists of a back plate 8 connected to a cylindrical side wall 10. The annular element 7 and casing 9 are formed from biocompatible materials and together form a sealed unit which is implantable subcutaneously in a patient.

A flow inlet 12 having a nozzle 14 projects radially from an end of the side wall 10 and a flow outlet 16 having a nozzle 18 projects radially from an opposite end of the side wall 10. It is contemplated that the relative position and orientation of the inlet 12 and outlet 16 may be varied to suit a particular application or a particular placement on or in a patient.

The annular element 7 of the body portion houses a valve comprising a closing element 20 in the form of a ball which selectively seals against a valve seat 22 formed in a radial inlet passage 26. The inlet passage 26 extends along a longitudinal axis x-x of the valve through the annular element 7 and opens into a feed passage 27. The inlet passage 26 and feed passage 27 are in fluid communication with a circumferential flow passage 32 defined between a radially inner face 34 of the side wall 10 and a groove 36 formed in the radially outer face of the annular element 7. The circumferential flow passage 32 is in fluid communication with an inlet bore 38 formed through the flow inlet nozzle 14.

A second circumferential passage 40 is defined between the radially inner face 34 of the side wall 10 and a second groove 42 formed in the radially outer face 30 of the annular element 7. The second circumferential passage 40 is in fluid communication with an outlet bore 44 formed through the flow outlet nozzle 18, and a pair of substantially radially disposed bores 46, 48 which extend from the radially inner face 28 to the radially outer face 30 of the annular element 7.

Referring to FIG. 1, the rotor 4 comprises a hub 50 housing the preload balls 5a to 5h in respective pockets 76a to 76h. The pockets 76a to 76h are shaped to accommodate the preload elements 5a to 5h with some play, and in particular to be sufficiently deep to allow the preload elements 5a to 5h to retract somewhat into the hub 50. This enables the preload element 5e to be withdrawn into the hub 50 and hence to allow the closing element 20 to lift away from the valve seat 22 so that cerebral spinal fluid can flow around the closing element 20.

The hub 50 is rotatably mounted within a bore 54 defined by the radially inner face 28 of the annular body 7. The hub 50 is fixed to a cruciform flange plate 56 which lies between the back plate 8 of the casing 9 and an axial end face 98 of the annular body 7.

The hub 50 is provided with a central bore 60 which houses a coil spring 62 and bearing element 64. The spring 62 bears on one end against a shoulder 66, defining a reduced diameter portion 68 of the central bore 60. At the other end, the spring 62 bears against the bearing element 64 and biases it against the back plate 8, such that a projection 70 formed centrally in the bearing element 64 engages the back plate 8 at a pivot point 72 about which the hub 50 can rotate.

A circumferential recess 78 is formed in a radially outer face of the hub 50, such that a circumferential flow channel 80 is defined between the annular element 7 and the hub 50. The flow channel 80 is in fluid communication with the radially disposed bores 46, 48.

Referring to FIG. 3, the cruciform flange plate 56 comprises four arms 56a to 56d. One of the arms 56a, is provided with a spring retainer opening 82. The radially outer ends of the arms 56a to 56d of the flange plate 56 lie closely adjacent to the radially inner face 34 of the side wall 10 of the casing 9. The radially inner face 34 comprises a plurality of arcuate camming surfaces 84a to 84h separated by axial grooves 86a to 86h. A first free end 88 of a first arm 90 of a bifurcated leaf spring 92 is engaged in the spring retaining opening 82, and a second arm 94 of the bifurcated leaf spring 92 is held against the radially inner face 34 owing to the tension in the leaf spring 92.

As best shown in FIG. 1, a locating pin 96 is fixed into a bore formed in one of the arms 56a of the cruciform flange plate 56. The locating pin 96 projects from an axial face 98 of the arm 56a and is aligned such that it can engage in one of a plurality of recesses 100a to 100h which each correspond to a respective pocket 76a to 76h.

In use, flexible tubes (not shown) are attached to the nozzles 14, 18 and the valve assembly 2 is implanted subcutaneously. The inlet tube attached to the inlet nozzle 14 is then connected to drain cerebral spinal fluid from the initial part of a shunt system, and the outlet tube attached to the outlet nozzle 18 is connected into the abdomen of a patient.

The valve assembly 2 is implanted such that with the patient standing, the inlet nozzle 14 lies directly above the outlet nozzle 18. In this orientation, the closing element 20 lies in the valve seat and whichever of the preload balls 5e is aligned with the closing element 20 rests on top of the closing element 20 and applies a preload to the valve. Consequently, the total preload acting to close the valve is provided by the combined mass of the closing element 20 and the preload ball 5e.

When the patient lies down, the mass of the closing element 20 and the mass of the preload ball 5e no longer act to bias the closing element 20 against the valve seat. Thus, the valve provides negligible effect on the flow of cerebral spinal fluid.

When the patient reclines, the vertical separation between head and the valve assembly 2 is less than when the patient is standing and greater than when the patient is lying down, so the pressure head of the cerebral spinal fluid due to the patient's posture is between the two extremes of standing and lying. These pressure changes are accommodated by the valve assembly 2 because as the patient reclines, the longitudinal axis x-x of the valve is inclined so that the mass of the closing element 20 and the preload ball 5a act to provide a closing force on the closing element which is related to the angle between the axis of the valve and a vertical axis. Thus, the preload on the valve automatically adjusts to compensate for the posture of the patient.

The preload applied to the closing element 20 can be changed by changing which of the preload balls 5a to 5h is aligned with the closing element 20. This is achieved by rotating the hub 50 relative to the casing 9. It will be appreciated that after the valve assembly 2 is implanted subcutaneously, it cannot then be accessed directly. Instead, a magnetic controller (not shown) is placed against the skin of the patient adjacent to the back plate 8 of the valve assembly 2. The magnet attracts the cruciform flange plate 56 which is made from magnetically responsive material, such as ferrous metal. This causes the flange plate 56 to be pulled away from the annular element 7, such that the pin 96 is withdrawn axially from the respective recess 100a to 100h. The magnet is then rotated, causing the flange plate 56 and hub 50 to rotate relative to the annular element 7 and the closing element 20. The flange plate 56 is rotated until the biasing element 5a to 5h of the desired weight is aligned with the closing element 20, and the pin 96 is aligned with the corresponding recess 100a to 100h whereupon the magnetic controller is removed.

When cerebral spinal fluid from the head of the patient enters the inlet nozzle 14 it passes down the inlet bore 38 into the circumferential flow passage 32, into the feed passage 27, and the inlet passage 26 until it is stopped by the closing element 20 sealing against the valve seat 22. When the pressure of the fluid exceeds the preload provided by the mass of the closing element 20 and whichever of the preload elements (5e in the illustrated embodiment) is adjacent the closing element 20, the closing element 20 will lift from the valve seat 22 and allow the fluid to pass the valve seat 22 and through the various flow paths in and around the rotary element 4 and from there into the circumferential flow channel 40 which connects to the exit 44.

The principle and mode of operation of this invention have been explained and illustrated in its preferred embodiment. However, it must be understood that this invention may be practiced otherwise than as specifically explained and illustrated, without departing from its spirit or scope.

What is claimed is:

1. A valve assembly for adjusting the flow of bodily fluid from one part of a human body to another, the valve assembly comprising:
    a body portion having a flow inlet and a flow outlet;
    a valve located in a flow path from the inlet to the outlet, the valve comprising a valve seat and a closing element, the closing element being adapted to seal against the valve seat; and
    a carrier element mounted within the body portion and having a plurality of pockets, each pocket housing a respective preload element, each preload element being of a different weight from that of the other preload elements,
    the carrier element being moveable relative to the body portion so as to align a preload element of a desired weight with the closing element, the self weight of the chosen preload element applying a preload to the closing element that is dependent on the orientation of the valve assembly.

2. A valve assembly as claimed in claim 1, wherein one or more of the closing element and the preload element are spherical.

3. A valve assembly as claimed in claim 1, wherein at least the portion of the closing element which engages the valve seat is spherical, planar, or conical.

4. A valve assembly as claimed in claim 1, wherein the preload element is substantially spherical, substantially cylindrical, or substantially rectilinear.

5. A valve assembly as claimed in claim 1, in which one or more of the closing element and the preload element are formed from high density material.

6. A valve assembly as claimed in claim 5, in which one or more of the closing element and the preload element are formed from tungsten carbide or tantalum.

7. A valve assembly as claimed in claim 1 wherein the carrier element comprises a rotor which is rotatable relative to the body portion.

8. A valve assembly as claimed in claim 1, wherein the carrier element is at least partially made from magnetically responsive material.

9. A valve assembly as claimed in claim 1, wherein the carrier element is biased towards the body portion.

10. A valve assembly as claimed in claim 9, wherein the carrier element is biased towards the body portion by a spring.

11. A valve assembly as claimed in claim 1, wherein one end face of the carrier element comprises a plurality of defined pole pieces which extend parallel to an axis of rotation of the rotor.

12. A valve assembly as claimed in claim 1, further comprising an indexing mechanism which acts between the body portion and the carrier element.

13. A valve assembly as claimed in claim 12, wherein the indexing mechanism comprises a sprung detent at the circumference of the carrier element, which sprung detent engages with corresponding formations on an inner diameter of the body portion.

14. A valve assembly as claimed in claim 13, wherein the sprung detent comprises a leaf spring.

15. A valve assembly as claimed in claim 1, further comprising a protrusion formed on one of the rotary element and the body portion, the protrusion engaging with any of a plurality of depressions formed in the other of the rotary element and the body portion.

16. A valve assembly as claimed in claim 15, wherein the protrusion is disengaged from the respective depression when the rotary element is moved axially away from the body portion, under the action of a magnetic force.

17. A valve assembly as claimed in claim 1, wherein the rotary element comprises a magnetic marker, such that the rotary position of the rotary element relative to the body portion can be detected by means of a compass type sensor device.

18. A flow control device comprising a valve assembly as claimed in claim 1 and a resistance valve, the valve assembly and the resistance valve sharing a common casing.

19. A flow control device comprising a valve assembly as claimed in claim 1 and a differential pressure valve, the valve assembly and differential pressure valve sharing a common casing.

20. A valve assembly as claimed in claim 1, wherein the valve assembly is made from bio-compatible material.

* * * * *